(12) United States Patent
Matsuda

(10) Patent No.: US 8,403,670 B2
(45) Date of Patent: Mar. 26, 2013

(54) METHOD FOR CREATING THREE-DIMENSIONAL DATA OF POSITION OF OUTER PERIPHERY AT OCCLUSAL SURFACE SIDE OF KEEPER WITH RESPECT TO ABUTMENT FOR IMPLANT

(75) Inventor: Yoshinori Matsuda, Itabashi-ku (JP)

(73) Assignee: GC Corporation, Tokyo (JP)

( * ) Notice: Subject to any disclaimer, the term of this patent is extended or adjusted under 35 U.S.C. 154(b) by 32 days.

(21) Appl. No.: 12/650,933

(22) Filed: Dec. 31, 2009

(65) Prior Publication Data
US 2010/0173265 A1 Jul. 8, 2010

(30) Foreign Application Priority Data
Jan. 6, 2009 (JP) .................................. 2009-001036

(51) Int. Cl.
*A61C 5/00* (2006.01)
(52) U.S. Cl. ....................................................... 433/215
(58) Field of Classification Search .................. 433/215, 433/214, 221; 703/1; 700/98, 97
See application file for complete search history.

(56) References Cited

U.S. PATENT DOCUMENTS

| | | | |
|---|---|---|---|
| 4,693,686 A | 9/1987 | Sendax | |
| 5,954,506 A | 9/1999 | Tanaka | |
| 6,203,325 B1 * | 3/2001 | Honkura et al. | 433/177 |
| 6,540,515 B1 | 4/2003 | Tanaka | |
| 7,708,557 B2 * | 5/2010 | Rubbert | 433/173 |
| 2005/0186540 A1 * | 8/2005 | Taub et al. | 433/223 |
| 2006/0019219 A1 * | 1/2006 | Saliger et al. | 433/173 |
| 2006/0275736 A1 * | 12/2006 | Wen et al. | 433/213 |
| 2007/0190493 A1 * | 8/2007 | Yamamoto et al. | 433/221 |
| 2008/0124676 A1 * | 5/2008 | Marotta | 433/174 |
| 2008/0248443 A1 * | 10/2008 | Chishti et al. | 433/24 |
| 2009/0117520 A1 | 5/2009 | Kikuchi | |

FOREIGN PATENT DOCUMENTS

| | | |
|---|---|---|
| JP | 2002-336277 | 11/2002 |
| JP | 2006-126004 | 5/2006 |

OTHER PUBLICATIONS

Extended European Search Report issued on Mar. 4, 2010 in the corresponding European Application No. 09016097.9.

* cited by examiner

*Primary Examiner* — Sunil K Singh
(74) *Attorney, Agent, or Firm* — Oblon, Spivak, McClelland, Maier & Neustadt, L.L.P.

(57) ABSTRACT

A method for creating three-dimensional data of a position of an outer periphery at the occlusal surface side of a keeper includes steps of placing a keeper analog having a reference plane in same shape as and in parallel to a surface at the occlusal surface side of a keeper to be embedded projectingly on an abutment model, three-dimensionally measuring an outside shape of the abutment model having the keeper analog, acquiring a normal vector and an outer periphery of the reference plane based on the measured three-dimensional data, moving the outer periphery to a position at the abutment model side by a height of the keeper analog from the reference plane along the normal vector and acquiring three-dimensional data of the outer periphery based on the position.

1 Claim, 3 Drawing Sheets

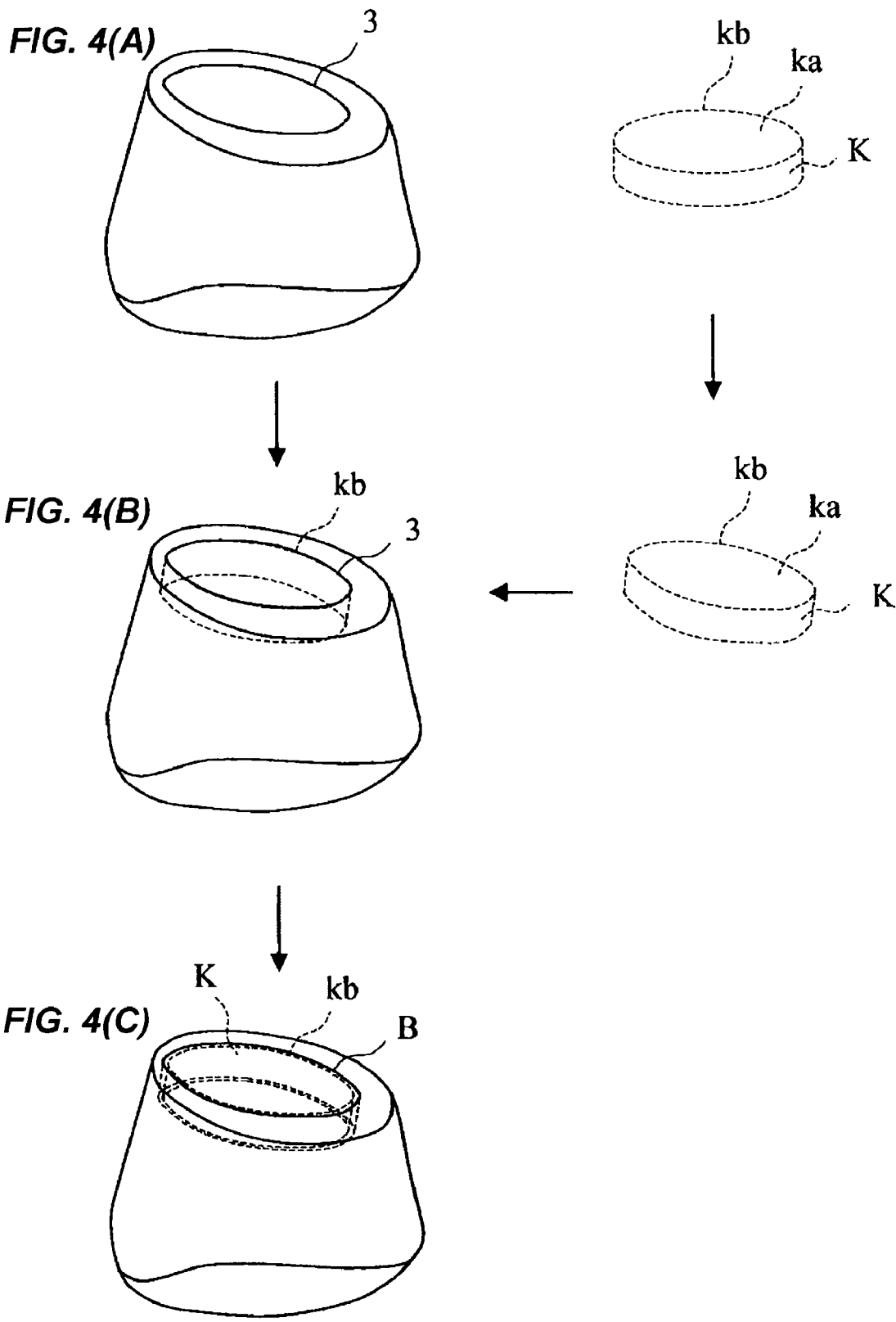

FIG. 5(A)
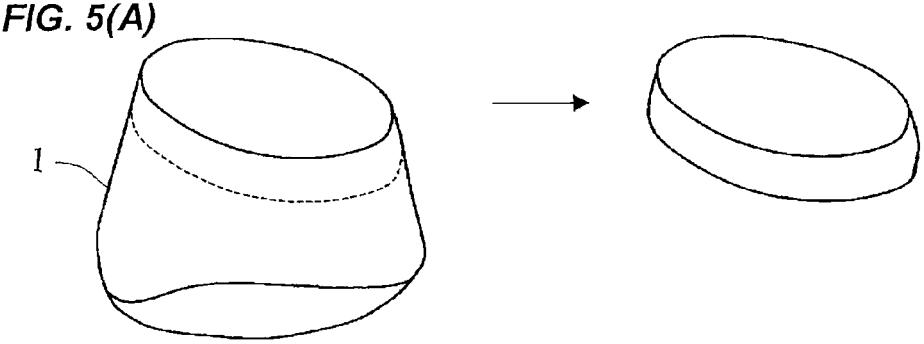
FIG. 5(B)
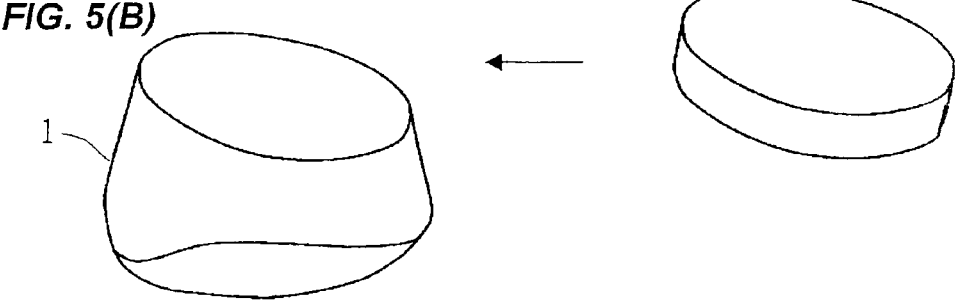
FIG. 5(C)
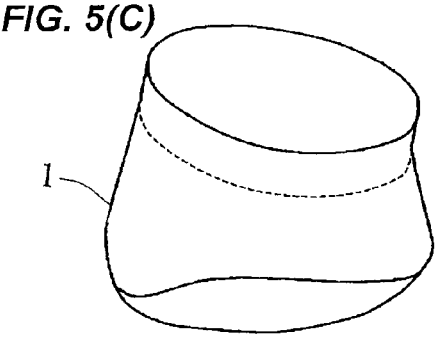

METHOD FOR CREATING THREE-DIMENSIONAL DATA OF POSITION OF OUTER PERIPHERY AT OCCLUSAL SURFACE SIDE OF KEEPER WITH RESPECT TO ABUTMENT FOR IMPLANT

BACKGROUND OF THE INVENTION

1. Field of the Invention

The present invention relates to a method for creating three-dimensional data of a position of an outer periphery at the occlusal surface side of a keeper with respect to an abutment for an implant, and the three-dimensional data is used when the three-dimensional data of the abutment for an implant is created.

2. Description of the Conventional Art

Conventionally, a dental technician manually performs almost all processes of an operation for producing a dental prosthesis, such as an abutment or the like, used for an implant treatment. Thus, there is a problem that a skill level of a dental technician greatly affects a quality of a dental prosthesis to be produced. Therefore, a dental CAD/CAM system has been developed in order to acquire a dental prosthesis with a stable quality. The dental CAD/CAM system produces the dental prosthesis by the steps of measuring a model of a produced dental prosthesis by a three-dimensional measuring apparatus, and cutting a cutting block for dentistries based on the measured three-dimensional data by an automatic cutting machine.

For example, Japanese Patent Applications Laid-Open Nos. 2006-126004 and 2002-336277 disclose the three-dimensional measuring apparatuses used for the dental CAD/CAM system. The three-dimensional measuring apparatuses perform noncontact type measurement using laser or contact type measurement using a probe.

However, there is a problem such that the measuring methods can hardly measure an accurate shape of a concave part. That is, a dead area is readily made in the concave part, and a measurement error easily occurs when the concave part is formed at a steep gradient from an outer surface. Therefore, the conventional apparatuses can hardly measure the accurate shape of a concave part, regardless of the noncontact type or contact type.

As a retaining device for fixing a partial or full denture in an oral cavity, a permanent magnetic structure and a magnetic attachment have been developed rapidly and used widely. The permanent magnetic structure is made by covering a permanent magnet with a corrosion-resistant alloy or the like. The magnetic attachment uses magnetic attraction power applied between a keeper made of a soft magnetic body and the magnetic attachment.

When the magnetic attachment is used as the retaining device, there are various advantages. The magnetic attachment does not have parts to be abraded and damaged, unlike a mechanical retaining device such as a clasp or the like. Thus, the magnetic attachment can keep retaining force for a long period of time without decreasing the retaining force. When rotational force is applied to the magnetic attachment, the magnetic attachment can make the force to release, so that excess load is not applied to a supporting base. Since the attaching and detaching direction of the magnetic attachment is not restricted, a denture can be easily designed and produced. Furthermore, since the attachment and detachment of the magnetic attachment are easy and the retaining device has not a complex shape, the magnetic attachment has excellent cleaning property.

When the magnetic attachment is used for an implant, a keeper is embedded in the oral cavity inner side of an abutment arranged on the oral cavity inner side of an implant fixture implanted in a lost tooth part of a patient, and the permanent magnetic structure is embedded in an alveolar ridge side inner surface of a denture. When the magnetic attachment is used as the retaining device, there are such advantages compared with an implant treatment using conventional retaining devices that a problem hardly occurs even if the rising direction of the implant fixture is somewhat bad, and the magnetic attachment does not need connection unlike a bar attachment, so that the rising position is not restricted. Therefore, an implant treatment using the magnetic attachment as a retaining device for a denture has been widely used in recent years.

However, in the implant treatment using the magnetic attachment as a retaining device for a denture, a process for boring a keeper embedding part for embedding a keeper in an abutment is needed, and the keeper embedding part is a concave part. Thus, when the three-dimensional measuring device measures an abutment model having the keeper embedding part, the device can hardly measure an accurate internal shape of the keeper embedding part. As a result, the dental CAD/CAM system can hardly produce an abutment having an accurate shape.

SUMMARY OF THE INVENTION

Problem to be Solved by the Invention

The present invention is to solve the aforementioned problems, and is directed to a method for creating three-dimensional data of a position of an outer periphery at the occlusal surface side of a keeper to be embedded in a keeper embedding part of an abutment for an implant. The three-dimensional data is used when creating three-dimensional data of the abutment for an implant arranged on the oral cavity inner side of an implant fixture implanted in a lost tooth part of a patient.

Means for Solving the Problem

Present inventors carried out earnest works to solve the aforementioned problems and, as a result, they found out the followings to complete the present invention. In a conventional technique, a gypsum model is produced based on an impression taken from a patient, where a fixture analog is implanted in the gypsum model at a position corresponding to a position in which an implant fixture is implanted. On the gypsum model, an abutment model is produced on a base material with a wax material, where the base material engages with the occlusal surface side of the fixture analog. A keeper embedding part, which is a concave part, is formed in the abutment model. However, it is extremely hard to three-dimensionally measure the keeper embedding part directly. Thus, the present inventors focused attention to that a keeper to be embedded in the keeper embedding part was put on the market together with a permanent magnetic structure, and the three-dimensional data of the keeper to be embedded was already given. If three-dimensional data of the position of the keeper to be embedded can be acquired, three-dimensional data of the accurate position of the keeper embedding part can be acquired by adding a predetermined gap or the like for an adhesive to the three-dimensional data of the position of the keeper. Further, as for the three-dimensional data of the position of the keeper to be embedded, it is not necessary to be newly measured by a three-dimensional measuring apparatus. Because, the previously given three-dimensional data of the shape of the keeper can be taken into a computer system of CAD or the like. If an outer periphery at the occlusal surface side, which is a part of the keeper is three-dimensionally measured and only the position of the outer periphery is determined, three-dimensional data of the position of the entire keeper can be accurately created from the previously given three-dimensional data of the shape by making the three-dimensional data of a position of an outer periphery at the occlusal surface side of the previously given three-dimensional data of the shape to agree with the three-dimensionally measured data of the position of the outer periphery at the occlusal surface side. Further, a keeper analog having a reference plane, which has the same shape as that of a surface at the occlusal surface side of the keeper and is parallel to the surface, is mounted on the abutment model, and is three-dimensionally measured. As a result, the outer periphery at the occlusal surface side of the keeper can be accurately measured at a projecting position. Furthermore, as for an easy method for performing the above-described processes, the following first and second steps can be performed. The first step is for placing the keeper analog projectingly on the abutment model so as to produce an abutment model having a keeper analog, placing the abutment model having the keeper analog on the three-dimensional measuring apparatus together with the base material, measuring three-dimensional data of an outside shape of the abutment model having the keeper analog, and acquiring a normal vector of the reference plane and an outer periphery of the reference plane of the keeper analog based on the measured three-dimensional data of the outside shape of the abutment model. The second step is for moving the outer periphery of the reference plane of the keeper analog to a position at the abutment model side by a height of the keeper analog from the reference plane of the keeper analog along the normal vector of the reference plane of the keeper analog, setting the position so moved to the abutment model side to be a position of the outer periphery at the occlusal surface side of the keeper, and thus acquiring three-dimensional data of the outer periphery at the occlusal surface side of the keeper. The method can accurately and easily create the three-dimensional data of a surface at the occlusal surface side of the keeper, where the method is a pre-process for creating the three-dimensional data of a final abutment for an implant.

An aspect of the present invention is a method for creating three-dimensional data of a position of an outer periphery at the occlusal surface side of a keeper to be embedded with respect to an abutment for an implant fixed at the occlusal surface side of an implant fixture, the method including steps of producing a gypsum model based on an impression taken from a patient, where a fixture analog is implanted at a position in the gypsum model corresponding to a position in which an implant fixture is implanted, producing an abutment model on a base material with a wax material on the gypsum model, where the base material engages with the occlusal surface side of the fixture analog, determining a direction of a surface at the occlusal surface side of a keeper to be embedded and a position of the surface at the occlusal surface side on the abutment model, placing a keeper analog on an abutment model projectingly from the determined position of the surface at the occlusal surface side of the keeper, where the keeper analog has a reference plane to be located at the side opposite to the abutment model and a surface to be located at the abutment model side, the reference plane has the same shape as a shape of the surface at the occlusal surface side of the keeper to be embedded, and the surface to be located at the abutment model side is parallel to the reference plane, so that the reference plane is made to be parallel to the surface at the occlusal surface side of the keeper to be embedded, placing the abutment model having the keeper analog on a three-dimensional measuring apparatus together with a base material, measuring three-dimensional data of an outside shape of the abutment model having the keeper analog, and creating the three-dimensional data of the position of the outer periphery at the occlusal surface side of the keeper to be based on the measured three-dimensional data of the outside shape of the abutment model having the keeper analog, Wherein the method for creating the three-dimensional data of the position of the outer periphery at the occlusal surface side of the keeper to be embedded with respect to the abutment for an implant further includes a first step of acquiring a normal vector of the reference plane and an outer periphery of the reference plane of the keeper analog, and a second step of moving the outer periphery of the reference plane of the keeper analog to a position at the abutment model side by a height of the keeper analog from the reference plane of the keeper analog along the normal vector of the reference plane of the keeper analog, setting the position to be a position of the outer periphery at the occlusal surface side of the keeper, and acquiring three-dimensional data of the outer periphery at the occlusal surface of the keeper.

Effect of the Invention

A method for creating three-dimensional data of a position of an outer periphery at an occlusal surface side of a keeper with respect to an abutment for an implant according to the present invention is a method for creating three-dimensional data of a position of an outer periphery at an occlusal surface side of a keeper to be embedded in a keeper embedding part, which is used when acquiring accurate three-dimensional data of the keeper embedding part of the abutment for an implant. The method includes steps of producing a gypsum model based on an impression taken from a patient, where a fixture analog is implanted at a position in the gypsum model corresponding to a position in which an implant fixture is implanted, producing an abutment model on a base material with a wax material on the gypsum model, where the base material engages with the occlusal surface side of the fixture analog, determining a direction of a surface at the occlusal surface side of a keeper to be embedded and a position of the surface at the occlusal surface side on the abutment model, placing a keeper analog on an abutment model projectingly from the determined position of the surface at the occlusal surface side of the keeper, where the keeper analog has a reference plane to be located at the side opposite to the abutment model and a surface to be located at the abutment model side, the reference plane has the same shape as a shape of the surface at the occlusal surface side of the keeper to be embedded, and the surface to be located at the abutment model side is parallel to the reference plane, so that the reference plane is made to be parallel to the surface at the occlusal surface side of the keeper to be embedded, placing abutment model having the keeper analog on a three-dimensional measuring apparatus together with a base material, measuring three-dimensional data of an outside shape of the abutment model having the keeper analog, and creating the three-dimensional data of the position of the outer periphery at the occlusal surface side of the keeper to be embedded, based on the measured three-dimensional data, wherein the method of the present invention further includes a first step of acquiring a normal vector of the reference plane and an outer periphery of the reference plane of the keeper analog, based on the measured three-dimensional data of the outside shape of the abutment model having the keeper analog, and a second step of moving the outer periphery of the reference plane of the keeper analog to a position at the abutment model side by a height of the keeper analog from the reference plane of the keeper analog along the normal vector of the reference plane of the keeper analog, setting the position to be a position of the outer periphery at the occlusal surface side of the keeper, and acquiring three-dimensional data of the outer periphery at the occlusal surface of the keeper. In the method, the keeper analog having the reference plane, which is to be located at the side opposite to the abutment model and has the same shape as that of the surface at the occlusal surface side of the keeper and is parallel to the surface at the occlusal surface side of the keeper, is mounted on the abutment model and is three-dimensionally measured. Thus, the measurement can be done at a projecting position where the three-dimensional measurement is easily performed. Then, the outer periphery of the reference plane of the keeper analog is made to move toward the abutment model side by a height of the keeper analog from the reference plane of the keeper analog along the normal vector of the reference plane of the keeper analog. Therefore, the three-dimensional data of the position of the outer periphery at the occlusal surface side of the keeper to be embedded can be accurately created. Further, based on the measured three-dimensional data of the position of the outer periphery at the occlusal surface side of keeper, three-dimensional data of the position of the entire keeper can be easily created by using the previously given three-dimensional data of the shape of entire keeper, which is previously taken into a computer system of CAD or the like as previously given data. When adding a predetermined gap or the like for an adhesive to the three-dimensional data of the position of the entire keeper to be embedded, three-dimensional data of the accurate position of the keeper embedding part can be acquired. Therefore, the three-dimensional data of the keeper embedding part, which is hard to be three-dimensionally measured directly by a conventional technique, can be accurately and easily acquired only by three-dimensionally measuring the position of the outer periphery at the occlusal surface side which is a part of the keeper to be embedded.

BRIEF DESCRIPTION OF DRAWINGS

FIGS. 4(A) to 4(C) are views illustrating a process for creating three-dimensional data of a keeper embedding part from the outer periphery at the occlusal surface side of the keeper in FIG. 3.

FIGS. 5(A) to 5(C) are views illustrating a process for preparing an outside shape of a portion at the occlusal surface side of an abutment to correct three-dimensional data of the abutment.

DETAILED DESCRIPTION OF PREFERRED EMBODIMENT

Figure 1:
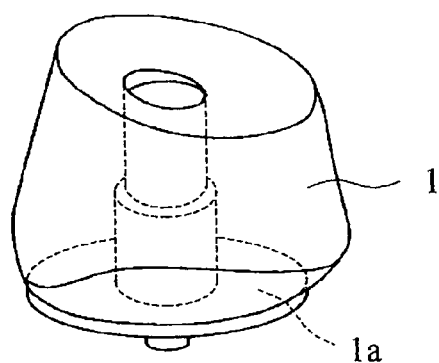
FIG. 1 is a perspective view illustrating an abutment model produced on a base material.

A method for creating three-dimensional data of a position of an outer periphery at the occlusal surface side of a keeper with respect to an abutment for an implant according to the present invention will be described in detail below with reference to the drawings.

In the drawings, a keeper embedding part B is formed in an abutment. A keeper K is to be embedded in the keeper embedding part B. A surface Ka is a surface at the occlusal surface side of the keeper K. An outer periphery Kb is an outer periphery at the occlusal surface side of the keeper K.

An abutment model 1 is produced on a base material 1a with a wax material on a gypsum model. The gypsum model is produced based on an impression taken from a patient, and includes a fixture analog implanted at a position corresponding to a position where an implant fixture is implanted. The base material 1a engages with an occlusal surface side of the fixture analog.

Since the abutment model 1 is produced on the gypsum model which is produced based an impression taken from a patient and includes the fixture analog implanted therein, the abutment model 1 can accurately reflect a margin line or the like. Therefore, using this abutment model 1, a position of an outer periphery at the occlusal surface side of the keeper to be embedded is introduced by a method for creating the three-dimensional data of a position of an outer periphery at the occlusal surface side of the keeper to be embedded according to the present invention. As a result, three-dimensional data of the keeper embedding part B, which very accurately reflects the positional relationship of the margin line or the like, can be created finally.

A keeper analog 2 is placed projectingly on the abutment model 1 after determining the direction of the surface Ka at the occlusal surface side of the keeper K to be embedded and the position of the surface Ka at the occlusal surface side on the abutment model 1. The keeper analog 2 has a reference plane 2a located at the side opposite to the abutment model 1, and has a surface located on the abutment model 1 side. The reference plane 2a has the same shape as a shape of the surface Ka at the occlusal surface side of the keeper K to be embedded. The surface located at the abutment model 1 side is parallel to the reference plane 2a.

The keeper analog 2 is placed on the abutment model 1 projectingly from the predetermined position of the surface Ka at the occlusal surface side of the keeper K, so that the reference plane 2a is made to be parallel to the surface Ka at the occlusal surface side of the keeper K. In the method of the present invention, the abutment model 1 having the keeper analog 2 is placed on a three-dimensional measuring apparatus together with a base material 1a, and is three-dimensionally measured. Based on the measured three-dimensional data of the outside shape, the method of the present invention creates the three-dimensional data of the position of the outer periphery Kb at the occlusal surface side of the keeper K to be embedded with respect to an abutment for an implant which is fixed at the occlusal surface side of an implant fixture.

A position 3 is a position to which an outer periphery 2ab of the reference plane 2a of the keeper analog 2 is moved to the abutment model 1 side by a height 2b of the keeper analog 2 from the reference plane 2a of the keeper analog 2 along a normal vector 2aa of the reference plane 2a of the keeper analog 2. Three-dimensional data of the position 3 is the three-dimensional data of the position of the outer periphery Kb at the occlusal surface side of the keeper K according to the present invention.

Figure 2:
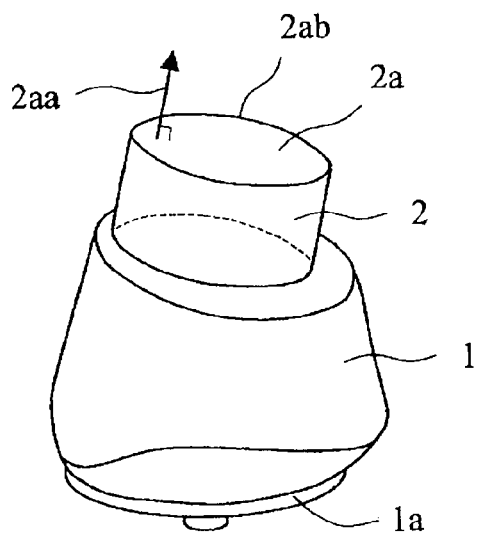
FIG. 2 is a perspective view illustrating a state that a keeper analog is placed projectingly on the abutment model in FIG. 1.

In order to actually create the three-dimensional data of the position of the outer periphery Kb at the occlusal surface side of the keeper K with respect to the abutment for an implant by the three-dimensional data creation method according to the present invention, the method includes the following processes. Firstly, as illustrated in FIG. 1, the abutment model 1 is produced on the base material 1a, which engages with the occlusal surface side of the fixture analog, with the wax material on the gypsum model. The direction of the surface Ka at the occlusal surface side of the keeper K to be embedded and the position of the surface Ka at the occlusal surface side are determined on the abutment model 1. Then, as illustrated in FIG. 2, the abutment model 1 is taken together with the base material 1a from the fixture analog, and the keeper analog 2 is placed on the abutment model 1 projectingly from the predetermined position of the surface Ka at the occlusal surface side of the keeper K. The keeper analog 2 has the reference plane 2a to be located at the side opposite to the abutment model 1 and the surface to be located at the abutment model 1 side. The reference plane 2a has the same shape as a shape of the surface Ka at the occlusal surface side of keeper K to be embedded, and the surface to be located at the abutment model 1 side is parallel to the reference plane 2a. The keeper analog 2 is placed on the abutment mode 1 so that the reference plane 2a is parallel to the surface Ka at the occlusal surface side of the keeper K to be embedded.

The three-dimensional measuring apparatus measures the entire abutment model 1 on which the keeper analog 2 is placed, to acquire the three-dimensional data of the entire shape of the abutment model 1 having the keeper analog 2. Based on the three-dimensional data, the normal vector 2aa of the reference plane 2a of the keeper analog 2 and the outer periphery 2ab of the reference plane 2a are acquired (the first step).

Figure 3:
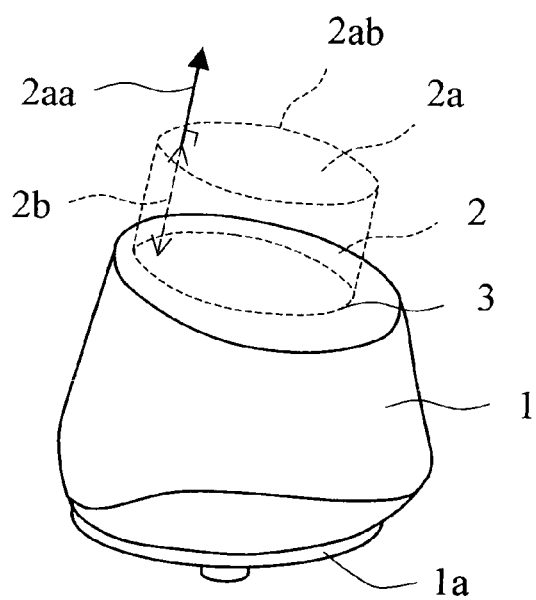
FIG. 3 is a view illustrating a position of an outer periphery at the occlusal surface side of a keeper in which a reference plane of the keeper analog in FIG. 2 is moved toward an abutment model side by a height of the keeper analog.

Next, the outer periphery 2ab of the reference plane 2a of the keeper analog 2 acquired in the first step is moved to the position 3 at the abutment model 1 side by the height 2b of the keeper analog 2 from the reference plane 2a of the keeper analog 2 along the normal vector 2aa of the reference plane 2a of the keeper analog 2, as illustrated in FIG. 3. The position 3 is set to be the position of the outer periphery Kb at the occlusal surface side of the keeper K, and the three-dimensional data of the outer periphery Kb at the occlusal surface side of the keeper K is thus acquired (the second step).

After the three-dimensional data of the outer periphery Kb at the occlusal surface side of the keeper K is created by the creation method according to the present invention as illustrated in FIG. 4 (A), the three-dimensional data of the keeper embedding part B is created as follows. The three-dimensional data of the accurate position of the keeper embedding part B can be acquired by making the previously given three-dimensional data of the shape of the entire keeper K to agree with the three-dimensional data of the outer periphery Kb at the occlusal surface side of the keeper K, which is acquired by the creation method according to the present invention, as illustrated in FIG. 4 (B), acquiring the three-dimensional data of the position of the entire keeper K from the previously given three-dimensional data of the shape, and adding a gap or the like for an adhesive to the acquired three-dimensional data as illustrated in FIG. 4 (C).

Accordingly, the final three-dimensional data of the abutment having the keeper embedding part B can be acquired from the measured three-dimensional data of the outside shape of the abutment model 1 and the three-dimensional data of the position of the keeper embedding part B, which are measured by the three-dimensional measuring apparatus. However, the final three-dimensional data of the abutment having the keeper embedding part B could be corrected as follows.

Even if the three-dimensional data of the outside shape of the abutment model 1 and the three-dimensional data of the position of the keeper embedding part B are accurately created, there may happen problems that a part of the keeper embedding part B could be located outside the abutment, or the thickness of the abutment of a part of the keeper embedding part B could be thinned. In addition, retaining force applied by magnetic force between the embedded keeper K and the permanent magnetic structure could not be fully acquired depending on the shape of the abutment surrounding the keeper embedding part B. In such a case, the three-dimensional data of the outside shape of the abutment, which is measured by the three-dimensional measuring apparatus, is necessarily corrected so as to prepare the shape of the abutment.

For example, when the three-dimensional data of the accurate position of the keeper embedding part B is created by the creation method according to the present invention, there happen cases that a part of the keeper embedding part B is located outside the abutment, or the thickness of the abutment of a part of the keeper embedding part B is thinned. In such a case, since the creation method according to the present invention has already acquired the three-dimensionally measured data of the outside shape of the abutment by the three-dimensional measuring apparatus, the outside shape of the abutment can be corrected by heaping up or the like on a computer so as to cover a part of the keeper embedding part B projecting to the outside of the abutment or thicken the thickness of the part having a thin thickness.

Further, for example, when a portion at the occlusal surface side of the abutment surrounding the keeper embedding part B is slightly tapered as illustrated in FIG. 5 (A) so that the magnetic force between the keeper K embedded in the keeper embedding part B and the permanent magnetic structure becomes weak easily, the tapered portion at the occlusal surface side of the abutment can be removed from the three-dimensionally measured data of the abutment, as illustrated in FIG. 5 (B) at the position moved toward the abutment side by the height of the keeper K to be embedded from the position of the outer periphery Kb at the occlusal surface side of the keeper K. Then, a pillar portion having the same cross section as the cross section of the removed portion is newly added to the occlusal surface side of the abutment, as illustrated in FIG. 5(C). As a result of this, the retaining force by the magnetic force between the keeper K and the permanent magnetic structure can be acquired easily.

Further, when the portion at the occlusal surface side of the abutment is removed as illustrated in FIG. 5 (B), the portion is not necessarily removed by the height of the keeper K to be embedded. If the portion at the occlusal surface side of the abutment can be removed so as not to reach a margin line of the abutment, the height of the portion to be removed can be lower or higher than the height of the keeper K.

The problem that a part of the keeper embedding part B is located outside the abutment and the problem that the thickness of the abutment of a part of the keeper embedding part B is thinned cannot be found out unless the three-dimensional data of the keeper embedding part B is created previously by the process illustrated in FIGS. 4(A) to 4(C). However, when the new pillar portion is formed at the occlusal surface side of the abutment, the three-dimensional data of the keeper embedding part B is not necessarily created previously. Thus, after the shape of the abutment is previously prepared by a process illustrated in FIGS. 5(A) to 5(C), and the three-dimensional measured data of the abutment is corrected, the three-dimensional data of the keeper embedding part B can be created by the process illustrated in FIGS. 4(A) to 4(C). Based on these three-dimensional data, the final three-dimensional data of the abutment can be acquired.

Accordingly, when the three-dimensional data of the outer periphery Kb at the occlusal surface side of the keeper K is created by the creation method according to the present invention, the three-dimensional data of the outer periphery Kb at the occlusal surface side of the keeper K can be accurately and easily created. Further, by using the three-dimensional data of the outer periphery Kb at the occlusal surface side of the keeper K, the three-dimensional data of the abutment having the keeper embedding part B, which is conventionally hard to be measured by a three-dimensional measuring apparatus, can be accurately and easily created.

What is claimed is:

1. A method for creating three-dimensional data of a position of an outer periphery at an occlusal surface side of a keeper member to be embedded with respect to an abutment for a dental implant, the method comprising steps of:

producing an abutment model having a reference surface for embedding a keeper embedding part with a wax material on a base material engaged with the occlusal surface side of a fixture analog;

placing a keeper analog on the reference surface for embedding the keeper embedding part in the abutment model projecting from a predetermined position of a surface at the occlusal surface side of the keeper member, wherein the keeper analog has a reference surface to be located at a side opposite to the abutment model and a surface to be located at the abutment model side, the reference surface has the same shape as a shape of the surface at the occlusal surface side of the keeper member to be embedded in the reference surface for embedding the keeper embedding part, and the surface to be located at the abutment model side is parallel to the reference surface, so that the reference surface is made to be parallel to the surface at the occlusal surface side of the keeper member to be embedded in the reference surface for embedding the keeper embedding part;

measuring three-dimensional data of an outside shape of the abutment model having the keeper analog; and creating the three-dimensional data of the position of the outer periphery at the occlusal surface side of the keeper member to be embedded in the reference surface for embedding the keeper embedding part based on the measured three-dimensional data of the outside shape of the abutment model having the keeper analog, wherein the method further comprises:

a first step of acquiring a normal vector of the reference surface and an outer periphery of the reference surface of the keeper analog, and a second step of moving the outer periphery of the reference surface of the keeper analog to a measurement position by a height of the keeper analog from the reference surface of the keeper analog along the normal vector of the reference surface of the keeper analog, replacing the three-dimensional data of the outer periphery at the occlusal surface side of the keeper analog to the three-dimensional data of the outer periphery representing on the reference surface for embedding the keeper embedding part.

* * * * *